(12) United States Patent
Wang et al.

(10) Patent No.: US 7,700,564 B2
(45) Date of Patent: *Apr. 20, 2010

(54) GLUTATHIONE BASED DELIVERY SYSTEM

(75) Inventors: Ae-June Wang, Hsinchu (TW);
Chi-Heng Jian, Yilan County (TW);
Shyh-Dar Li, Miaoli County (TW);
Yi-Fong Lin, Taipei County (TW);
Shih-Jr Liu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/263,885

(22) Filed: Nov. 3, 2008

(65) Prior Publication Data

US 2009/0060991 A1 Mar. 5, 2009

Related U.S. Application Data

(63) Continuation of application No. 11/303,934, filed on Dec. 19, 2005, now Pat. No. 7,446,096.

(51) Int. Cl.
*A61K 38/06* (2006.01)
*A61K 51/08* (2006.01)

(52) U.S. Cl. .................. 514/18; 424/1.21; 530/331; 977/773

(58) Field of Classification Search ............... None
See application file for complete search history.

(56) References Cited

U.S. PATENT DOCUMENTS

| 5,080,904 | A | 1/1992 | Iga et al. | |
|---|---|---|---|---|
| 5,695,751 | A | 12/1997 | Friedman et al. | |
| 6,627,732 | B1 | 9/2003 | Sakon et al. | |
| 6,653,331 | B2 | 11/2003 | Zhao et al. | |
| 7,446,096 | B2 * | 11/2008 | Wang et al. | 514/18 |
| 2003/0109555 | A1 | 6/2003 | Zhao et al. | |

FOREIGN PATENT DOCUMENTS

| EP | 1 072 608 A1 | 1/2001 |
|---|---|---|
| FR | 2 627 385 A | 8/1989 |
| JP | 63-2922 A | 1/1988 |
| WO | WO-99/54346 A1 | 10/1999 |
| WO | WO 00/28977 | 5/2000 |

OTHER PUBLICATIONS

Banks et al., Life Sciences, vol. 59, No. 23, 1996, pp. 1923-1943.
Zlokovic et al., Biochemical and Biophysical Research Communications, vol. 201, No. 1, May 30, 1994, pp. 402-408.
Kannan et al., The Journal of Biological Chemistry, vol. 271, No. 16, Apr. 19, 1996, pp. 9754-9758.
Kannan et al., Journal of Neurochemistry, vol. 73, No. 1, 1999, pp. 390-399.
Kannan et al., Elsevier Science B.V., 2000, pp. 374-382.
Zlokovic, Pharmaceutical Research, vol. 12, No. 10, 1995, pp. 1395-1406.
"Liposome carrier for liver disease treatment—contains N-higher acyl glutathione as base material", Derwent, XP002322756, abstract (Jan. 7, 1988).
Kiwada et al., Chemical and Pharmaceutical Bulletin, Pharmaceutical Society of Japan, Tokyo, JP., vol. 35, No. 7, pp. 2935-2942, XP002276804 (Jul. 7, 1987).
Suntres et al., Journal of Pharmacy and Pharmacology, London, GB, vol. 46, No. 1, pp. 23-28, XP001105800 (Jan. 1, 1994).
Jurima-Romet et al., Journal of Pharmacy and Pharmacology, London, GB, vol. 43, No. 1, pp. 6-10, XP001105806 (1991).
Sugiyama et al., Journal of Controlled Release, Elsevier, Amsterdam, NL, vol. 62, No. 1-2, pp. 179-186, XP004363015 (Nov. 1, 1999).
Kabanov, et al., 1982, Institute of Physical Chemistry, Academy of Sciences USSR, Moscow, pp. 771-775.

* cited by examiner

*Primary Examiner*—Andrew D Kosar
*Assistant Examiner*—Satyanarayana R Gudibande
(74) *Attorney, Agent, or Firm*—Birch, Stewart, Kolasch & Birch, LLP

(57) ABSTRACT

A delivery system. The delivery system includes a carrier or an active compound and a glutathione or a glutathione derivative grafted thereon. The invention also provides a compound including a moiety comprising a vitamin E derivative or a phospholipid derivative, a polyethylene glycol (PEG) or a polyethylene glycol derivative bonded thereto, and a glutathione (GSH) or a glutathione derivative bonded to the polyethylene glycol or the polyethylene glycol derivative.

13 Claims, 6 Drawing Sheets

GLUTATHIONE BASED DELIVERY SYSTEM

This application is a Continuation of application Ser. No. 11/303,934 filed on Dec. 19, 2005, which is issued as U.S. Pat. No. 7,446,096 B2 on Nov. 4, 2008 and for which priority is claimed under 35 U.S.C. § 120, the entire contents of which are hereby incorporated by reference.

BACKGROUND

The invention relates to a biological delivery system, and more specifically to a glutathione based delivery system.

The blood brain barrier (BBB) is composed of brain endothelial cells capable of blocking foreign substances, such as toxin, due to the tight junction therebetween. Hydrophobic or low-molecular-weight molecules, however, can pass through the BBB via passive diffusion.

Nevertheless, active compounds, such as hydrophilic protein drugs for treating cerebral or nervous diseases and analgesic peptide drugs acting on the central nervous system, cannot enter brain tissue thereby due to their large molecular weight or hydrophilicity, resulting in decomposition by enzymes.

Current researches forward various methods of allowing active compounds to pass through the BBB, including structural modification to increase hydrophobicity of drugs, absorption-mediated transport (AMT) allowing positive-charged carriers to pass via charge absorption, carrier-mediated transcytosis (CMT) allowing hydrophilic metal ions such as $Na^+$ and $K^+$, di-peptides, tri-peptides or glucose to pass via transporters, and receptor-mediated transcytosis (RMT) allowing macro molecules such as insulin, transferrin, or low-density lipoprotein (LDL) to pass via transcytosis.

Glutathione (GSH) is an endogenous antioxidant. If its concentration in serum is insufficient, some nervous diseases, such as chronic fatigue syndrome (CFS), may occur.

In 1988, Kiwada Hiroshi provided a liposome capable of accumulation in liver comprising a N-acylglutathione such as N-palmitoylglutathione and a phospholipid such as phosphotidylcholine to target and treat liver diseases recited in JP63002922.

In 1994, Berislav V. Zlokovic asserted that glutathione (GSH) reaches and passes through the BBB of a guinea pig via a special route, such as GSH-transporter, without decomposition.

In 1995, Berislav V. Zlokovic asserted that glutathione (GSH) exists in brain astrocyte and endothelial cells with millimolar concentration.

In 1995, Ram Kannan asserted that GSH uptake depends on $Na^+$ concentration. If $Na^+$ concentration is low, GSH uptake from brain endothelial cells may be inhibited. He also pointed Na-dependent GSH transporter located on the luminal side of the BBB manages GSH uptake and Na-independent GSH transporter located on the luminal side of the BBB manages efflux of GSH. Additionally, Kannan built a rat hepatic canalicular GSH transporter (RcGSHT) system using the brains of mice and guinea pigs to analyze cDNA fragments 5, 7, and 11. The results indicate that fragment 7 represents Na-dependent GSH transporter and fragments 5 and 11 represent Na-dependent GSH transporter.

In 1999, Ram Kannan built a mouse brain endothelial cell line (MBEC-4) model simulating BBB situations. The model proved that Na-dependent GSH transporter is located on the luminal side of the MBEC-4 cell.

In 2000, Ram Kannan asserted that GSH passes through the BBB via Na-dependent GSH transporter in human cerebrovascular endothelial cells (HCEC) and Na-dependent GSH transporter exists in the luminal plasma membrane of HCEC.

In 2003, Zhao Zhiyang provided an anti-cancer pro-drug bonded with glutathione s-transferase (GST)/glutathione (GSH) by sulfonamide covalent bonds to target and treat specific cancer cells after broken of the sulfonamide bonds recited in US2003109555. This modification can protect amino groups of drugs, increase solubility thereof, and alter absorption and distribution thereof in body.

SUMMARY

The invention provides a delivery system comprising a carrier or an active compound and a glutathione or a glutathione derivative grafted thereon.

The invention also provides a compound comprising a moiety comprising a vitamin E derivative or a phospholipid derivative, a polyethylene glycol (PEG) or a polyethylene glycol derivative bonded thereto, and a glutathione (GSH) or a glutathione derivative bonded to the polyethylene glycol or the polyethylene glycol derivative.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the subsequent detailed description and the accompanying drawings, which are given by way of illustration only, and thus are not limitative of the present invention, and wherein.

DETAILED DESCRIPTION

Figure 1:
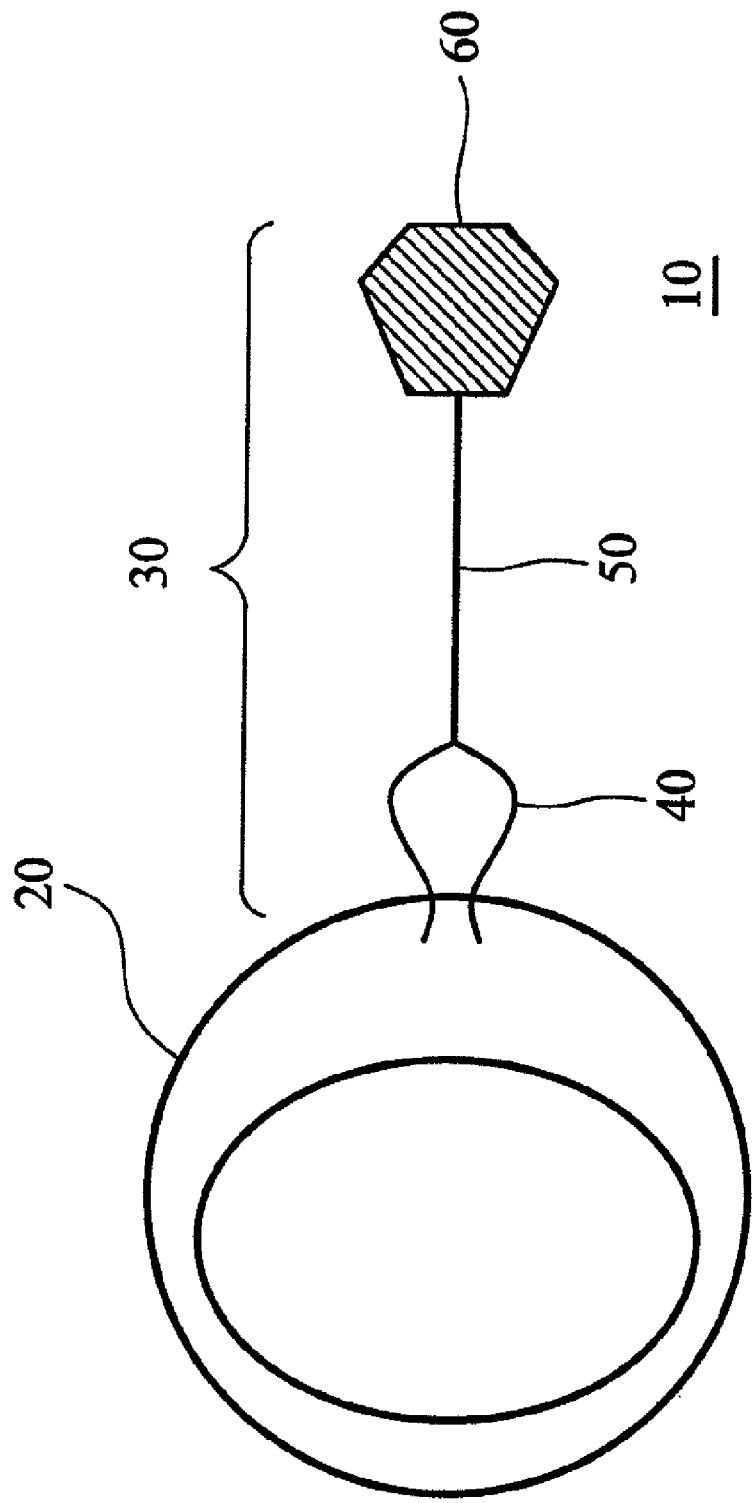
FIG. 1 shows a delivery system of the invention.

The invention provides a delivery system comprising a carrier or an active compound and a glutathione or a glutathione derivative grafted thereon. The carrier may comprise nanoparticle, polymeric nanoparticle, solid liquid nanoparticle, polymeric micelle, liposome, microemulsion, or liquid-based nanoparticle. The liposome comprises at least one of lecithin such as soy lecithin and hydrogenated lecithin such as hydrogenated soy lecithin.

The liposome may further comprise cholesterol, water-soluble vitamin E, or octadecyl amine to increase serum resistance or charge amounts. The molar composition ratio of the liposome may be 0.5-100% of lecithin or hydrogenated lecithin, 0.005-75% of cholesterol or water-soluble vitamin E, 0.001-25% of octadecyl amine.

Additionally, the carrier may encapsulate the active compound in an encapsulation efficiency of about 0.5-100%. The active compound may comprise small molecule compounds such as gabapentin, peptides such as enkephalin, proteins, DNA plasmids, oligonucleotides, or gene fragments and have a molar ratio of about 0.0005-95% in the carrier.

The targeted carrier or the active compound may target on glutathione transporters of organs such as heart, lung, liver, kidney, or blood brain barrier.

Specifically, the active compound can pass through the blood-brain-barrier (BBB), such as brain endothelial cells, with the targeted carrier and has a cell penetration rate of about 0.01-100%.

The invention also provides a compound comprising a moiety comprising a vitamin E derivative or a phospholipid derivative, a polyethylene glycol (PEG) or a polyethylene glycol derivative bonded thereto, and a glutathione (GSH) or a glutathione derivative bonded to the polyethylene glycol or the polyethylene glycol derivative.

The vitamin E derivative comprises tocopherol derivatives or tocotrienol derivatives and may be α-tocopherol, β-tocopherol, γ-tocopherol, δ-tocopherol, α-tocotrienol, β-tocotrienol, γ-tocotrienol, δ-tocotrienol, α-tocopherol succinate, β-tocopherol succinate, γ-tocopherol succinate, δ-tocopherol succinate, α-tocotrienol succinate, β-tocotrienol succinate, γ-tocotrienol succinate, β-tocotrienol succinate, α-tocopherol acetate, β-tocopherol acetate, γ-tocopherol acetate, δ-tocopherol acetate, α-tocotrienol acetate, β-tocotrienol acetate, γ-tocotrienol acetate, δ-tocotrienol acetate, α-tocopherol nicotinate, β-tocopherol nicotinate, γ-tocopherol nicotinate, δ-tocopherol nicotinate, α-tocotrienol nicotinate, β-tocotrienol nicotinate, γ-tocotrienol nicotinate, δ-tocotrienol nicotinate, α-tocopherol phosphate, β-tocopherol phosphate, γ-tocopherol phosphate, δ-tocopherol phosphate, α-tocotrienol phosphate, β-tocotrienol phosphate, γ-tocotrienol phosphate, or δ-tocotrienol phosphate.

The phorpholipid derivative may have the following formulae comprising $R_1$-$A_1$- (I) or

(II)

In formula (I), $A_1$ is sphingosine and $R_1$ may comprise octanoyl or palmitoyl. In formula (II), $A_2$ is phosphoethanoamine and $R_2$ may comprise myristoyl, palmitoyl, stearoyl, or oleoyl.

The polyethylene glycol (PEG) or the polyethylene glycol derivative has a polymerization number (n) of about 6-210. The molecular weight of the polyethylene glycol (PEG) or the polyethylene glycol derivative may be altered with various vitamin E derivatives or phospholipid derivatives. For example, when PEG or its derivative is bonded to vitamin E derivatives, it may have a molecular weight of about 300-10000, when PEG or its derivative is bonded to the phospholipid derivatives represented by formula (I), it may have a molecular weight of about 750-5000, and when PEG or its derivative is bonded to the phospholipid derivatives represented by formula (II), it may have a molecular weight of about 350-5000.

The polyethylene glycol derivative may comprise carboxylic acid, maleimide, PDP, amide, or biotin.

Referring to FIG. 1, the delivery system of the invention is illustrated. The delivery system 10 comprises a liposome 20 and a ligand 30 grafted thereon. The ligand 30 comprises a moiety 40 comprising a vitamin E derivative or a phospholipid derivative, a polyethylene glycol (PEG) or a polyethylene glycol derivative 50 bonded thereto, and a glutathione (GSH) or a glutathione derivative 60 bonded to the polyethylene glycol and the polyethylene glycol derivative.

Active compounds, such as proteins, peptides, or small molecules, transported by the targeted carrier with a novel glutathione (GSH) ligand provided by the invention can effectively pass through blood-brain-barrier by carrier-mediated transcytosis (CMT) or receptor-mediated transcytosis (RMT) to treat cerebral or nervous diseases.

EXAMPLE 1

Preparation of TPGS-Glutathione

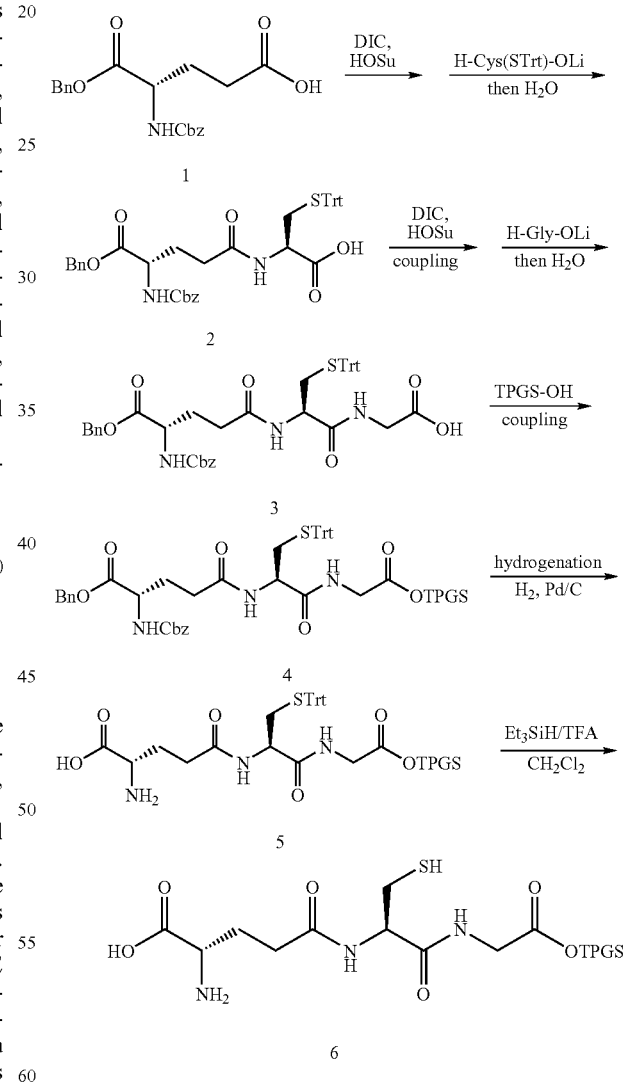

A stirred solution of N-Cbz Benzyl amino acid (N-Cbz Glutamine, 1.0 equiv) and N-hydroxysuccinimide (HOSu, 1.0 equiv) in DME (15 mL) was cooled to 0° C. Dicyclohexylcarbodiimide (DIC, 1.0 equiv) was added and stirred at this temperature for 4 hr. The reaction mixture was allowed to stand for 2 hr in a refrigerator and then filtered.

As expected, the pure compound was obtained in excellent yield (98%) after filtration of the dicyclohexylurea (DCU) formed and evaporation of the solvent. The residue was triturated in Et$_2$O/hexanes, filtered out, and then dried in vacuo to afford a white solid.

The (+)-S-tritylcysteine lithium salt (H-Cys(STrt)-OLi, 1.0 equiv) and sodium carbonate (Na$_2$CO$_3$, 5.0 equiv) were dissolved in water (15 mL), and then acetonitrile (CH$_3$CN) was added followed by the intermediated product obtained in Step-2. The mixture was vigorously stirred at room temperature for 3-6 hr until the TLC analysis indicated the absence of intermediated product in Step-2. The solution was washed with water (2*100 mL) and the organic phase was dried with Na$_2$SO$_4$, filtered, and concentrated in vacuo to afford the compound 2.

A stirred solution of compound 2 and N-hydroxysuccinimide (HOSu, 1.0 equiv) in DME (15 mL) was cooled to 0° C. Dicyclohexylcarbodiimide (DIC, 1.0 equiv) was added and stirred at this temperature for 4 hr. The reaction mixture was allowed to stand for 2 hr in a refrigerator and then filtered.

After the DCU and solvent was removed, the glycine lithium salt (H-Gly-OLi, 1.0 equiv) and sodium carbonate (Na$_2$CO$_3$, 5.0 equiv) were dissolved in water (15 mL), and then acetonitrile (CH$_3$CN) was added followed by the intermediated product obtained in Step-4. The mixture was vigorously stirred at room temperature for 3-6 hr until the TLC analysis indicated the absence of intermediated product in Step-4. The solution was washed with water (2*100 mL) and the organic phase was dried with Na$_2$SO$_4$, filtered, and concentrated in vacuo to afford the compound 3.

The d-alpha tocopheryl polyethylene glycol 1000 succinate (TPGS-OH) was coupling with compound 3 via esterification to afford the compound 4.

The compound 4 in methanol (100 mL) was added 10% Pd—C (0.2 times the weight of protected tripeptide-TPGS). The suspension was stirred at room temperature for 16 hr under a balloon filled with hydrogen. The suspension was filtered through Celite and evaporated, and the residue was crystallized from ethanol. Then, the compound 5 was obtained.

Triethylsilane (Et$_3$SiH) and TFA-mediated deprotection of compound 5 in the presence of CH$_2$Cl$_2$ provided the compound 6 (that is GSH-TPGS).

Preparation of Met-Enkephalin Carrier Solution 0.5 g lipid containing 83.2% soybean phosphatidylcholine (SPC), 4.2% α-tocopherol succinate PEG 1500 (TPGS), 4.2% glutathione-TPGS (GSH-TPGS), and 8.4% cholesterol was placed in a 12.5 mL ZrO$_2$ mortar. Appropriate amounts of met-enkephalin were dissolved in 10 mM phosphate solution with pH7.4 to form a 4% drug solution. 0.5 mL drug solution and five ZrO$_2$ beads (10 mm of diameter) were then added to the mortar and ground with 500 rpm for one hour to form a sticky cream. Next, 0.2 g sticky cream and 1.8 mL phosphate solution (10 mM, pH7.4) were added to a 10 mL flask to hydrate under room temperature for one hour to form a carrier solution containing liposomes encapsulating met-enkephalin. The concentration of met-enkephalin in a liposome was 0.56 mg/mL. The encapsulation efficiency thereof was 33.3%. The mean diameter of the carrier was 173.1 nm as well as the polydispersity index (PI) was 0.243.

EXAMPLES 2-6

Preparation methods of examples 2-6 are similar to example 1. The distinctions therebetween are the various carrier compositions. Please see Tables 1 and 2.

TABLE 1

| | (Molar ratio) | | | | | | |
|---|---|---|---|---|---|---|---|
| Example | Soy lecithin | H-soy lecithin | Cholesterol | TPGS | TPGS-GSH | Octadecyl amine | Met-enkephalin |
| 2 | 10 | — | 1 | — | 1 | — | 0.48 |
| 3 | 10 | — | 1 | — | 1 | 1 | 1.60 |
| 4 | 9 | 1 | 1 | 0.5 | 0.5 | — | 1.60 |
| 5 | 9 | 1 | 1 | 0.75 | 0.25 | — | 1.60 |
| 6 | 9 | 1 | 1 | — | 1 | — | 1.60 |

TABLE 2

| Example | Mean diameter (nm) | PI | Met-enkephalin concentration (mg/mL) | Encapsulation efficiency (%) |
|---|---|---|---|---|
| 2 | 162.7 | 0.227 | 0.56 | 31.70 |
| 3 | 161.4 | 0.046 | 4.00 | 70.33 |
| 4 | 214.1 | 0.003 | 3.25 | 68.85 |
| 5 | 165.3 | 0.137 | 3.40 | 68.48 |
| 6 | 214.5 | 0.116 | 3.99 | 80.78 |

EXAMPLE 7

Preparation of Gabapentin Carrier Solution 0.5 g lipid containing 83.2% soybean phosphatidylcholine (SPC), 4.2% α-tocopherol succinate PEG 1500 (TPGS), 4.2% glutathione-TPGS (GSH-TPGS), and 8.4% cholesterol was placed in a 12.5 mL ZrO$_2$ mortar. Appropriate amounts of gabapentin were dissolved in 10 mM phosphate solution with pH7.4 to form a 10% drug solution. 0.5 mL drug solution and five ZrO$_2$ beads (10 mm of diameter) were then added to the mortar and ground with 500 rpm for one hour to form a sticky cream. Next, 0.2 g sticky cream and 1.8 mL phosphate solution (10 mM, pH7.4) were added to a 10 mL flask to hydrate under room temperature for one hour to form a carrier solution containing liposomes encapsulating gabapentin. The concentration of gabapentin in a liposome was 1.08 mg/mL. The encapsulation efficiency thereof was 35.7%. The mean diameter of the carrier was 147.7 nm as well as the polydispersity index (PI) was 0.157.

COMPARATIVE EXAMPLE 1

Preparation of Met-Enkephalin Carrier Solution 0.5 g lipid containing 83.2% soybean phosphatidylcholine (SPC), 8.4% α-tocopherol succinate PEG 1500 (TPGS), and 8.4% cholesterol was placed in a 12.5 mL ZrO$_2$ mortar.

Appropriate amounts of met-enkephalin were dissolved in 10 mM phosphate solution with pH7.4 to form a 4% drug solution. 0.5 mL drug solution and five $ZrO_2$ beads (10 mm of diameter) were then added to the mortar and ground with 500 rpm for one hour to form a sticky cream. Next, 0.2 g sticky cream and 1.8 mL phosphate solution (10 mM, pH7.4) were added to a 10 mL flask to hydrate under room temperature for one hour to form a carrier solution containing liposomes encapsulating met-enkephalin. The concentration of met-enkephalin in a liposome was 0.57 mg/mL. The encapsulation efficiency thereof was 31.1%. The mean diameter of the carrier was 164.1 nm as well as the polydispersity index (PI) was 0.281.

COMPARATIVE EXAMPLES 2-3

Preparation methods of comparative examples 2-3 are similar to comparative example 1. The distinctions therebetween are the various carrier compositions. Please see Tables 3 and 4.

TABLE 3

| Comparative example | (Molar ratio) | | | | | |
|---|---|---|---|---|---|---|
| | Soy lecithin | H-soy lecithin | Cholesterol | TPGS | Octadecyl amine | Met-enkephalin |
| 2 | 10 | — | 1 | 1 | 1 | 1.60 |
| 3 | 9 | 1 | 1 | 1 | — | 1.60 |

TABLE 4

| Comparative Example | Mean diameter (nm) | PI | Met-enkephalin concentration (mg/ml) | Encapsulation efficiency (%) |
|---|---|---|---|---|
| 2 | 159.7 | 0.103 | 3.58 | 70.17 |
| 3 | 149.0 | 0.168 | 3.22 | 69.67 |

COMPARATIVE EXAMPLE 4

Preparation of Gabapentin Carrier Solution 0.5 g lipid containing 83.2% soybean phosphatidylcholine (SPC), 8.4% α-tocopherol succinate PEG 1500 (TPGS), and 8.4% cholesterol was placed in a 12.5 mL $ZrO_2$ mortar. Appropriate amounts of gabapentin were dissolved in 10 mM phosphate solution with pH7.4 to form a 10% drug solution. 0.5 mL drug solution and five $ZrO_2$ beads (10 mm of diameter) were then added to the mortar and ground with 500 rpm for one hour to form a sticky cream. Next, 0.2 g sticky cream and 1.8 mL phosphate solution (10 mM, pH7.4) were added to a 10 mL flask to hydrate under room temperature for one hour to form a carrier solution containing liposomes encapsulating gabapentin. The concentration of gabapentin in a liposome was 1.17 mg/mL. The encapsulation efficiency thereof was 38.5%. The mean diameter of the carrier was 155.8 nm as well as the polydispersity index (PI) was 0.186.

In Vitro Penetration Rate Test 1 of Met-Enkephalin Liposome

The penetration rate of met-enkephalin was measured using a RBE4/glioma cell model simulating BBB situations. The test results of examples 1-2 (containing glutathione) and comparative example 1 (without glutathione) are compared in Table 5.

TABLE 5

| Example | Drug dose (μg) | Penetration rate (%) | SD |
|---|---|---|---|
| Comparative Example 1 | 182.6 | 3.4 | 0.6 |
| Example 1 | 167.7 | 9.8 | 1.3 |
| Example 2 | 165.2 | 9.8 | 1.2 |

The results indicate that examples 1 and 2 have an apparently higher penetration rate (9.8%) of about 2.82 times greater than comparative example 1 (3.4%).

In Vitro Penetration Rate Test 2 of Met-Enkephalin Liposome

The penetration rate of met-enkephalin was measured using a RBE4/glioma cell model simulating BBB situations. The test results of example 3 (containing glutathione) and comparative example 2 (without glutathione) are compared in Table 6.

TABLE 6

| Example | Drug dose (μg) | Penetration rate (%) | SD |
|---|---|---|---|
| Comparative Example 2 | 250.0 | 3.55 | 0.36 |
| Example 3 | 250.0 | 6.99 | 1.43 |
| Example 3 (glutathione added) | 250.0 | 0.25 | 0.03 |

The results indicate that example 3 has an apparently higher penetration rate (6.99%) of about 1.96 times greater than comparative example 2 (3.55%). Additionally, if cells were cultured with glutathione for 30 min before example 3 was performed, the penetration rate thereof was lowered by 0.25% due to the addition of glutathione which occupied the glutathione transporter of the cells to block binding of carriers, reducing drug penetration through the BBB. The result proves that the glutathione carrier provided by the invention passes through the BBB via glutathione ligand/transportor binding to induce carrier-mediated transcytosis (CMT) or receptor-mediated transcytosis (RMT).

Hot-Plate Test of Met-Enkephalin Liposome

Figure 2:
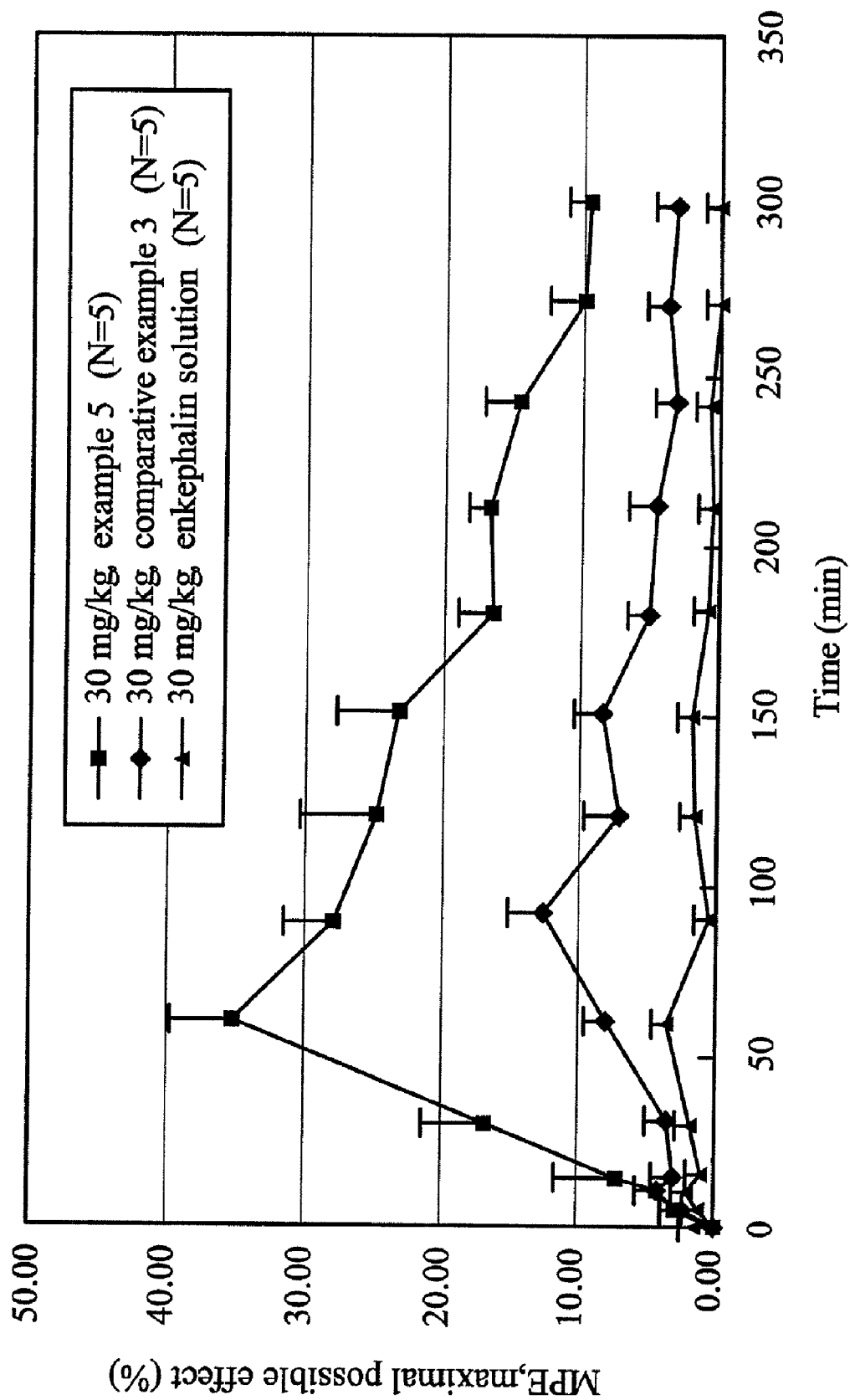
FIG. 2 shows maximal possible effect (MPE) of various met-enkephalin carriers of the invention.
Figure 3:
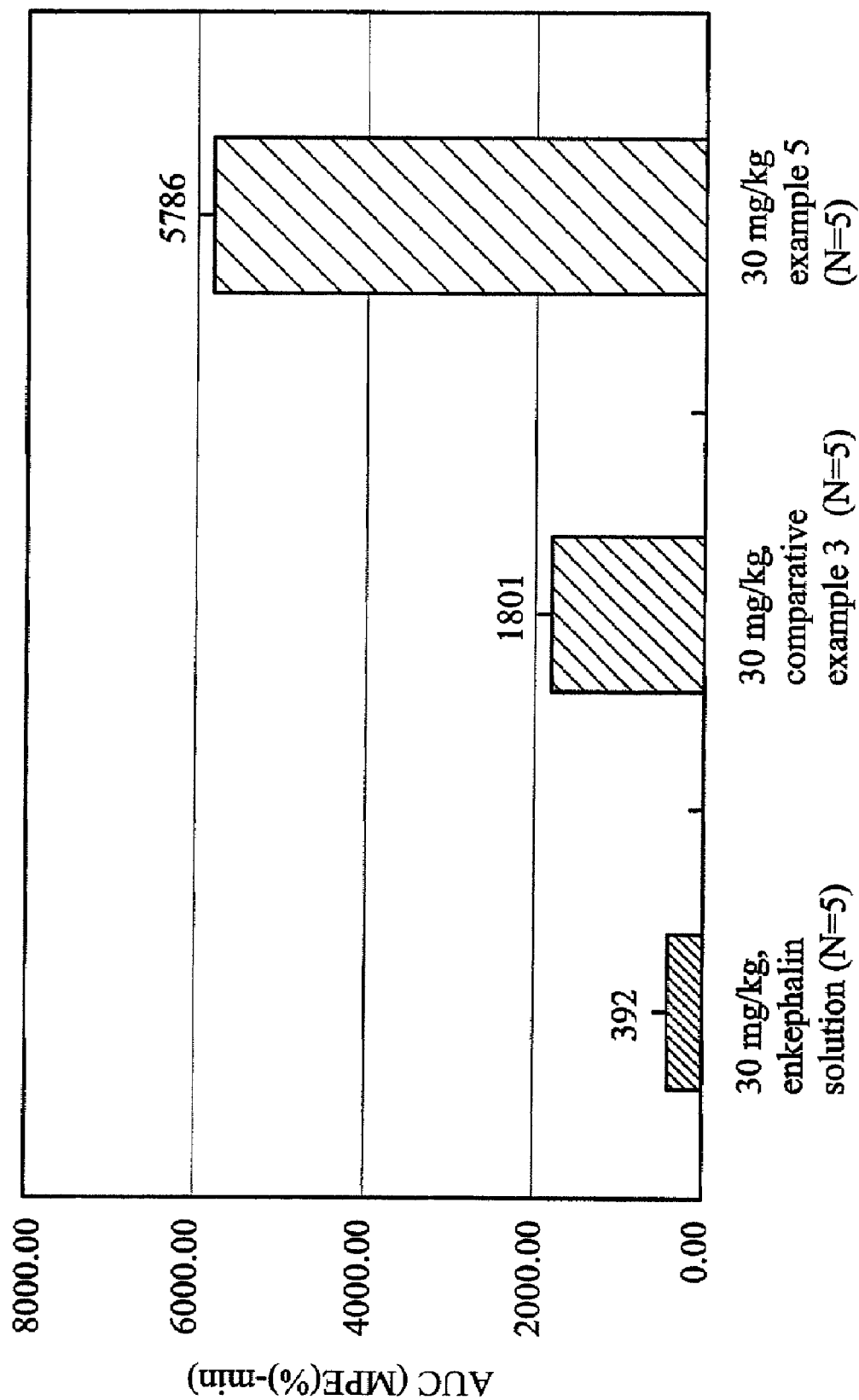
FIG. 3 shows area under curve (AUC) of various met-enkephalin carriers of the invention.

After a laboratory mouse on a 55° C. hot plate was intravenously injected, the analgesic effect on heat-induced pain was evaluated. Referring to FIG. 2, for carriers without glutathione (comparative example 3), 90 min after injection, the maximal possible effect (MPE) of a 30 mg/mL dose was 13%. For carriers containing glutathione (example 5), 60 min after injection, the maximal possible effect (MPE) of 30 mg/mL dose was 37%. Referring to FIG. 3, according to the area under curve (AUC), example 5 provides 3.2 times the analgesic effect of comparative example 3 and 14.7 times the met-enkephalin solution. Thus, drugs can be safely carried by the carrier with glutathione ligand to pass through the BBB to achieve analgesic effect.

Hot-Plate Test of Gabapentin Liposome

Figure 4:
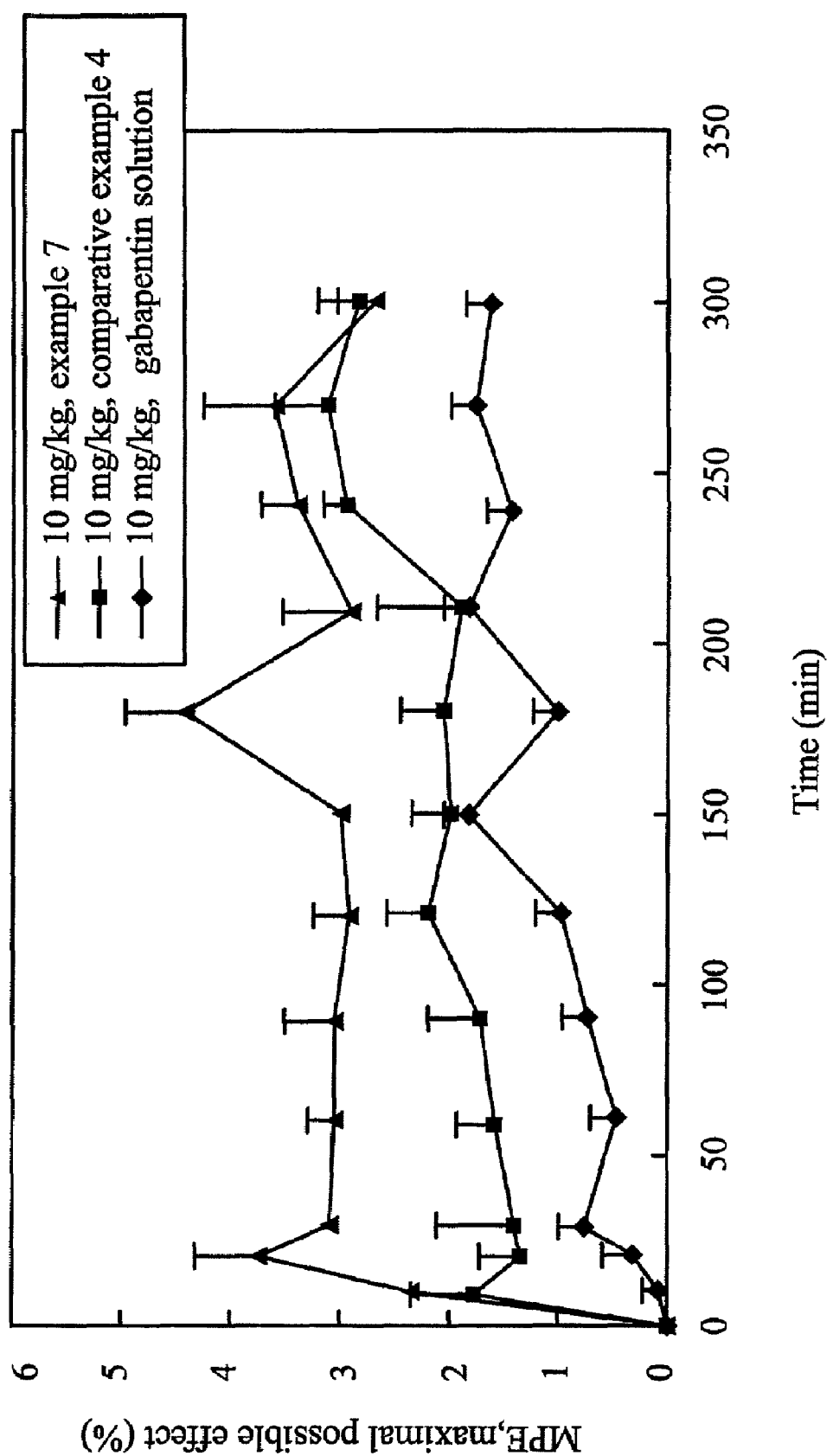
FIG. 4 shows maximal possible effect (MPE) of various gabapentin carriers of the invention.
Figure 5:
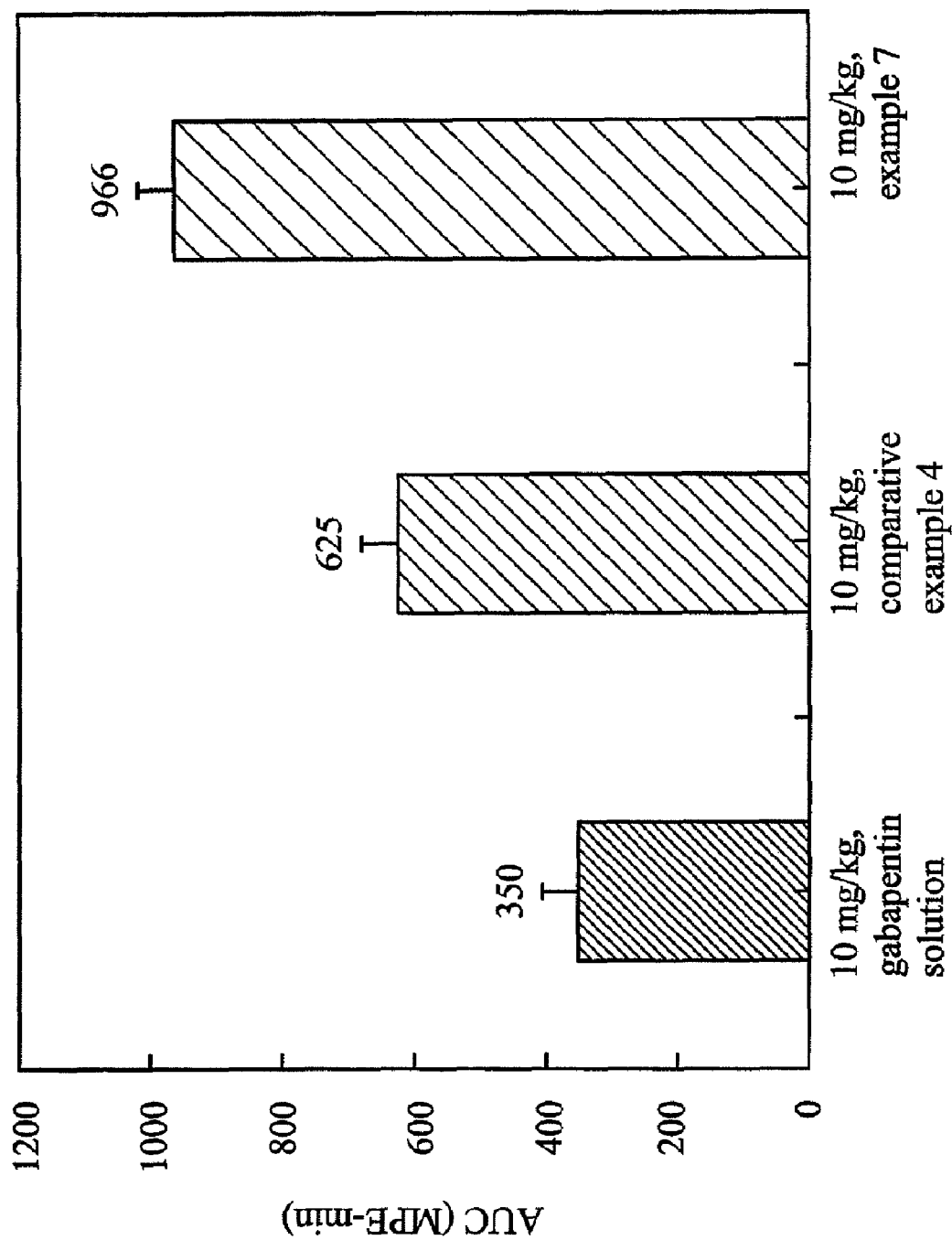
FIG. 5 shows area under curve (AUC) of various gabapentin carriers of the invention.

After a laboratory mouse on a 55° C. hot plate was intravenously injected, the analgesic effect on heat-induced pain was evaluated. Referring to FIG. 4, for carriers without glutathione (comparative example 4), 270 min after injection, the maximal possible effect (MPE) of a 10 mg/mL dose was 3.15%. For carriers containing glutathione (example 7), 180 min after injection, the maximal possible effect (MPE) of a 10 mg/mL dose was 4.47%. Referring to FIG. 5, according to the area under curve (AUC), example 7 provides 1.54 times the analgesic effect of comparative example 4 ($p<0.005$) and 2.76 times the gabapentin solution ($p<0.0005$). Thus, drugs can be safely carried by the carrier with glutathione ligand to pass through the BBB to achieve analgesic effect.

Serum Stability Test of Met-Enkephalin Liposome

Figure 6:
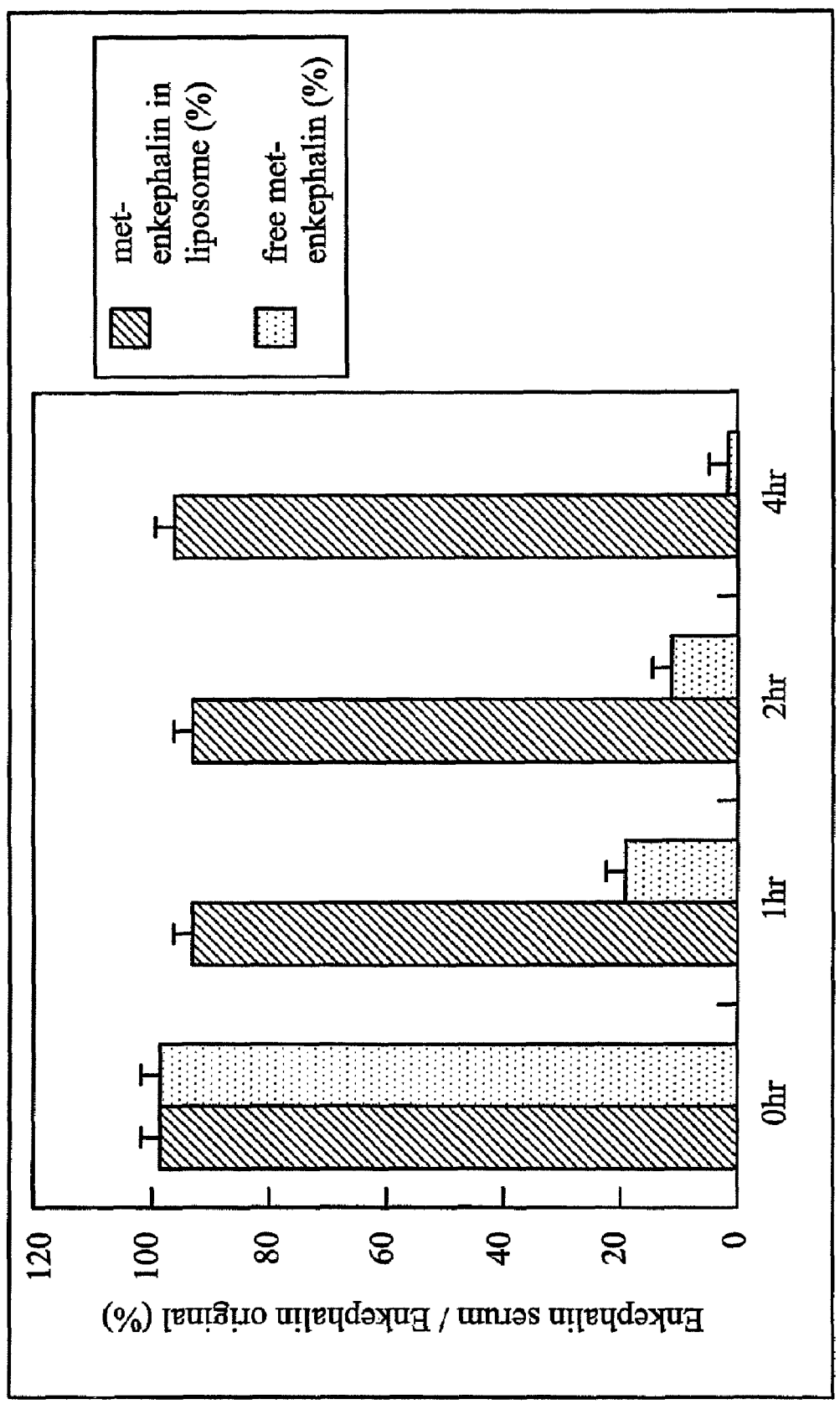
FIG. 6 shows serum stability of free met-enkephalin and met-enkephalin in liposomes.

The carriers provided by example 5 and fetal bovine serum (FBS) were mixed with 1:1 (v/v) to form a solution. After being placed in a 37° C. water bath for 0, 1, 2, and 4 hours, respectively, the solution was analyzed by gel filtration (Sephrox CL-4B, 75 mm×120 mm) and measured residual concentration of met-enkephalin in liposomes. The results are shown in FIG. 6.

The results indicate that the concentration of met-enkephalin in liposomes remains 93% above. However, residual concentration of free met-enkephalin decreases to 2%. It is clear that the carrier provided by the invention has high serum resistance.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of achieving an analgesic effect, comprising: administering a delivery system to a subject in need thereof, said delivery system comprising:
a carrier which comprises glutathione,
wherein said glutathione is covalently bound to polyethylene glycol,
wherein the polyethylene glycol is covalently bound to vitamin E or a phospholipid, and
wherein the vitamin E or phospholipid is intercalated into the carrier such that the glutathione is on an outside surface of the carrier.

2. The method of claim 1, wherein the active compound has a penetration ratio for brain endothelial cells of about 0.01-100%.

3. The method of claim 1, wherein the carrier further comprises an active compound encapsulated thereinto, and wherein the active compound comprises small molecule compounds, peptides, proteins, DNA plasmids, oligonucleotides, or gene fragments.

4. The method of claim 1, wherein the carrier is a nanoparticle, a polymeric nanoparticle, a solid liquid nanoparticle, a polymeric micelle, a liposome, a microemulsion, or a liquid-based nanoparticle.

5. The method of claim 4, wherein the liposome comprises at least one of lecithin and hydrogenated lecithin, and wherein the liposome further optionally comprises cholesterol, water-soluble vitamin E, or octadecyl amine.

6. The method of claim 1, wherein the phospholipid has formula (I):

wherein $A_1$ is sphingosine and $R_1$ comprises octanoyl or palmitoyl.

7. The method of claim 1, wherein the phospholipid has formula (II):

wherein $A_2$ is phosphoethanoamine and $R_2$ comprises myristoyl, palmitoyl, stearoyl, or oleoyl.

8. The method of claim 1, wherein the polyethylene glycol has a molecular weight of about 300-10000 and is covalently bound to vitamin E.

9. The method of claim 6, wherein the polyethylene glycol has a molecular weight of about 750-5000 and is covalently bound to the phospholipid of formula (I).

10. The method of claim 7, wherein the polyethylene glycol has a molecular weight of about 350-5000 and is covalently bound to the phospholipid of formula (II).

11. The method of claim 1, wherein the polyethylene glycol has a polymerization number (n) of about 6-210.

12. A method of achieving an analgesic effect, comprising: administering a delivery system to a subject in need thereof, said delivery system comprising:
a carrier; and
glutathione,
wherein said carrier is a nanoparticle, a polymeric nanoparticle, a solid liquid nanoparticle, a polymeric micelle, a liposome, microemulsion, or a liquid-based nanoparticle, and
wherein said glutathione is covalently bound to polyethylene glycol, wherein the polyethylene glycol is covalently bound to vitamin E or a phospholipid, and wherein the vitamin E or phospholipid is intercalated into the carrier, such that the glutathione is on an outside surface of the carrier.

13. A method of achieving an analgesic effect, comprising: administering a delivery system to a subject in need thereof, said delivery system comprising:
a carrier comprising a glutathione derivative,
wherein said carrier is selected from group consisting of: a nanoparticle, a polymeric nanoparticle, a solid liquid nanoparticle, a polymeric micelle, a liposome, a microemulsion, and a liquid-based nanoparticle,
wherein said glutathione derivative is glutathione covalently bound to a polyethylene glycol derivative which is itself covalently bound to a vitamin E derivative or a phospholipid,
wherein said polyethylene glycol derivative is selected from the group consisting of: polyethylene glycol, a polyethylene glycol comprising carboxylic acid, a polyethylene glycol comprising maleimide, a polyethylene glycol comprising an amide, and a polyethylene glycol comprising biotin,
wherein said vitamin E derivative is selected from the group consisting of:
vitamin E, α-tocopherol, β-tocopherol, γ-tocopherol, δ-tocopherol, α-tocotrienol, β-tocotrienol, γ-tocotrienol, δ-tocotrienol, α-tocopherol succinate, β-tocopherol succinate, γ-tocopherol succinate, δ-tocopherol succinate, α-tocotrienol succinate, β-tocotrienol succinate, γ-tocotrienol succinate, δ-tocotrienol succinate, α-tocopherol acetate, β- tocopherol acetate, γ-tocopherol acetate, δ-tocopherol acetate, α-tocotrienol acetate, β-tocotrienol acetate, γ-tocotrienol acetate, δ-tocotrienol acetate, α-tocopherol nicotinate, β- tocopherol nicotinate, γ-tocopherol nicotinate, δ-tocopherol nicotinate, α-tocotrienol nicotinate, βtocotrienol nicotinate, γ-tocotrienol nicotinate, δ-tocotrienol nicotinate, α-tocopherol phosphate, β-tocopherol phosphate, γ-tocopherol phosphate, δ-tocopherol phosphate, α-tocotrienol phosphate, β-tocotrienol phosphate, γ-tocotrienol phosphate, or δ-tocotrienol phosphate, and
wherein the phospholipid has the structure of formula (II):

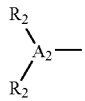

(II)

wherein $A_2$ is phosphoethanoamine and $R_2$ is selected from the group consisting of: myristoyl, palmitoyl, stearoyl and oleoyl, wherein the glutathione is on an outside surface of the carrier.

* * * * *